United States Patent
Ichimura

(10) Patent No.: US 9,597,057 B2
(45) Date of Patent: Mar. 21, 2017

(54) PORTABLE ULTRASONIC DIAGNOSTIC DEVICE

(71) Applicant: HITACHI ALOKA MEDICAL, LTD., Mitaka-shi, Tokyo (JP)

(72) Inventor: Masaru Ichimura, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 170 days.

(21) Appl. No.: 14/374,174

(22) PCT Filed: Feb. 4, 2013

(86) PCT No.: PCT/JP2013/052494
§ 371 (c)(1),
(2) Date: Jul. 23, 2014

(87) PCT Pub. No.: WO2013/145866
PCT Pub. Date: Oct. 3, 2013

(65) Prior Publication Data
US 2015/0038841 A1 Feb. 5, 2015

(30) Foreign Application Priority Data
Mar. 30, 2012 (JP) .................. 2012-080927

(51) Int. Cl.
*A61B 8/00* (2006.01)
*G06F 1/16* (2006.01)

(52) U.S. Cl.
CPC ............ *A61B 8/462* (2013.01); *A61B 8/4427* (2013.01); *G06F 1/1681* (2013.01)

(58) Field of Classification Search
CPC ...... A61B 8/462; A61B 8/4427; G06F 1/1681
(Continued)

(56) References Cited

U.S. PATENT DOCUMENTS

| 5,924,988 A * | 7/1999 | Burris | A61B 8/00 600/437 |
| 2004/0179332 A1* | 9/2004 | Smith | A61B 90/36 361/679.41 |

(Continued)

FOREIGN PATENT DOCUMENTS

| CN | 201061540 Y | 5/2008 |
| CN | 101334684 A | 12/2008 |

(Continued)

OTHER PUBLICATIONS

International Search Report dated May 7, 2013 issued in corresponding application No. PCT/JP2013/052494.

(Continued)

*Primary Examiner* — Sanjay Cattungal
(74) *Attorney, Agent, or Firm* — Westerman, Hattori, Daniels & Adrian, LLP

(57) ABSTRACT

A portable ultrasonic diagnostic device having a tilt function and turning function for a display panel, wherein a display housing provided with the display panel is supported on a main housing by a biaxial hinge mechanism in order to prevent damage or the like to each of the parts of the device. The biaxial hinge mechanism includes a tilt function for tilting the display housing about a horizontal tilt rotational shaft, and a turning function for turning the display housing about a vertical turning shaft. Provided to the tilt rotational shaft is a mechanism for restricting tilt rotation in the direction for closing the display housing in places other than a predetermined position in the direction of rotation of the turning shaft of the display housing, and releasing the restriction of the tilt rotation only at the predetermined position.

13 Claims, 9 Drawing Sheets

(58) Field of Classification Search
USPC .................................................. 600/437–469
See application file for complete search history.

(56) References Cited

U.S. PATENT DOCUMENTS

| | | | |
|---|---|---|---|
| 2009/0002927 A1 | 1/2009 | Iijima et al. | |
| 2011/0166451 A1* | 7/2011 | Blaivas | A61B 17/282 600/439 |
| 2012/0316438 A1 | 12/2012 | Ninomiya et al. | |
| 2013/0131501 A1* | 5/2013 | Blaivas | A61B 8/14 600/424 |
| 2013/0131502 A1* | 5/2013 | Blaivas | A61B 8/14 600/424 |
| 2014/0360274 A1* | 12/2014 | Cho | A61B 8/4427 73/644 |

FOREIGN PATENT DOCUMENTS

| | | |
|---|---|---|
| JP | 8-270638 A | 10/1996 |
| JP | 2010-162107 A | 7/2010 |
| WO | 2011/122099 A1 | 10/2011 |

OTHER PUBLICATIONS

Notification Concerning Transmittal of the International Preliminary Report on Patentability (Chapter I of the Patent Cooperation Treaty) (Forms PCT/IB/326) of the International Application No. PCT/JP2013/052494 mailed Oct. 9, 2014 with Forms PCT/IB/373, PCT/IB/338 and PCT/ISA237; w/English Translation.
Office Action dated Dec. 30, 2015, issued in counterpart Chinese Application No. 201380018212.6, with English translation. (10 pages).

\* cited by examiner (a)

(b)

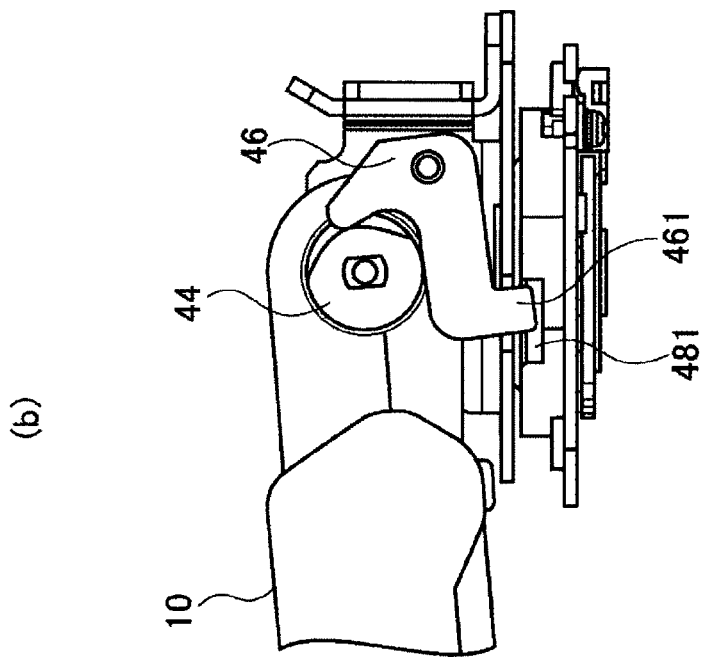
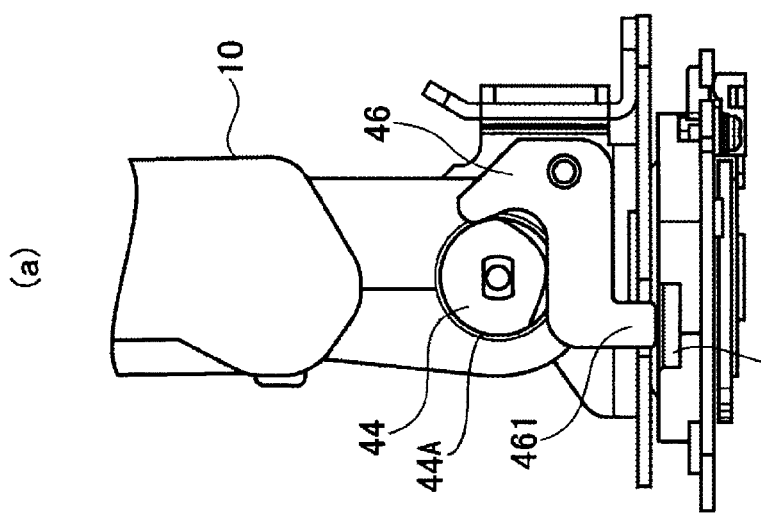
FIG. 9(a)
FIG. 9(b)

PORTABLE ULTRASONIC DIAGNOSTIC DEVICE

TECHNICAL FIELD

The present invention relates to a portable ultrasonic diagnostic device, and more particularly, to a portable ultrasonic diagnostic device having a structure in which a display housing including a display panel is foldable with respect to a body.

BACKGROUND ART

Portable ultrasonic diagnostic devices are widely spread as relatively simple and non-invasive medical image diagnostic devices. Various types of portable ultrasonic diagnostic devices which can be used not only in hospital examination rooms but also in patient rooms or outside hospitals have been developed. For example, note-type devices having a structure in which a display panel for displaying captured images or the like and an operation panel for inputting commands required for ultrasonic measurements connected to each other in an openable/closable manner at one edge have been in practical use.

Portable ultrasonic diagnostic devices are advantageous because ultrasonic images can be obtained in real time during measurement such that patients under examination can check their own ultrasonic images at the site. In order to make use of this advantage, there have been proposed devices having a display panel which is not only openable and closable but also pivotable such that patients and others in addition to an operator can view the display panel (Patent Documents 1 and 2).

In the portable ultrasonic diagnostic device described in Patent Document 1, a display housing including a display panel is connected by an arm which is pivotable with respect to a body, and thereby the display panel is not only openable and closable but also pivotable in 360 degrees about a pivot axis. Further, in the portable ultrasonic diagnostic device described in Patent Document 2, an operation panel housing provided with an operation panel and a display housing provided with a display panel are connected to one edge of a body housing such that the operation panel housing and the display housing are respectively openable and closable; and by applying a biaxial hinge mechanism in which a pivot shaft is fixed to a bearing portion of a rotation shaft for open/close movement of the display housing, pivoting of the display housing is enabled in addition to opening, closing, and tilting of the display housing.

RELATED ART DOCUMENTS

Patent Documents

Patent Document 1: JP 2010-162107 A
Patent Document 2: International Publication No. WO 2011/122099

DISCLOSURE OF THE INVENTION

Problems to be Solved by the Invention

Although usability has been improved by providing a pivot function to a mobile ultrasonic diagnostic device as described above, a new problem has arisen. Because, in conventional mechanisms, a display housing can be closed even when the display panel is at a position pivoted to a certain degree from a predetermined position at which the display panel surface of the display housing faces front of an operation panel, the display housing may interfere with an element on a body housing or a connecting portion between the body housing and the operation panel housing when the display panel is tilted beyond a certain degree. Because an examination using a portable ultrasonic diagnostic device is often performed in a dark room, when the display housing is closed as described above without checking the pivoted position of the display panel, the display housing may collide with other elements, thereby causing damage to the display panel or other problems.

The present invention is provided to solve the above problem. An object of the present invention is to provide a portable ultrasonic diagnostic device having a tilt function of a display panel such that the display panel can be tilted without causing damage or the like to other elements of the device.

Means for Solving the Problems

In the present invention, in order to achieve the above object, a tilt limit mechanism is provided with a tilt shaft for tilting a display panel housing in a portable ultrasonic diagnosis device with a display panel tilt function. The tilt limit mechanism releases the tilt limit only when the display panel housing is at a predetermined position in a pivotable direction of a pivot shaft, while prevents tilting elsewhere.

Advantage of the Invention

According to the present invention, a display panel can be tilted without causing damage or the like to any part of a device.

BRIEF DESCRIPTION OF THE DRAWINGS

FIGS. 9 (a) and (b) are diagrams showing movement of a tilt limit mechanism.

BEST MODE FOR CARRYING OUT THE INVENTION

Figure 1:
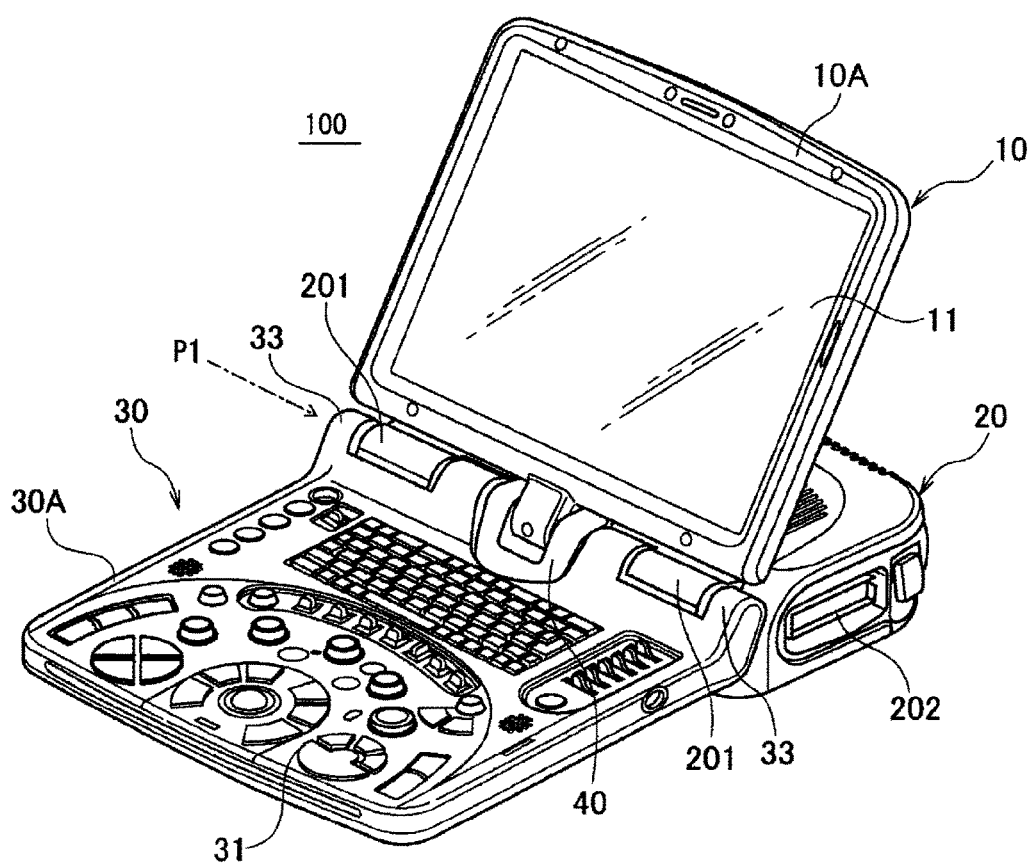
FIG. 1 is an overall perspective diagram of one embodiment of a portable ultrasonic diagnostic device according to the present invention.
Figure 2:
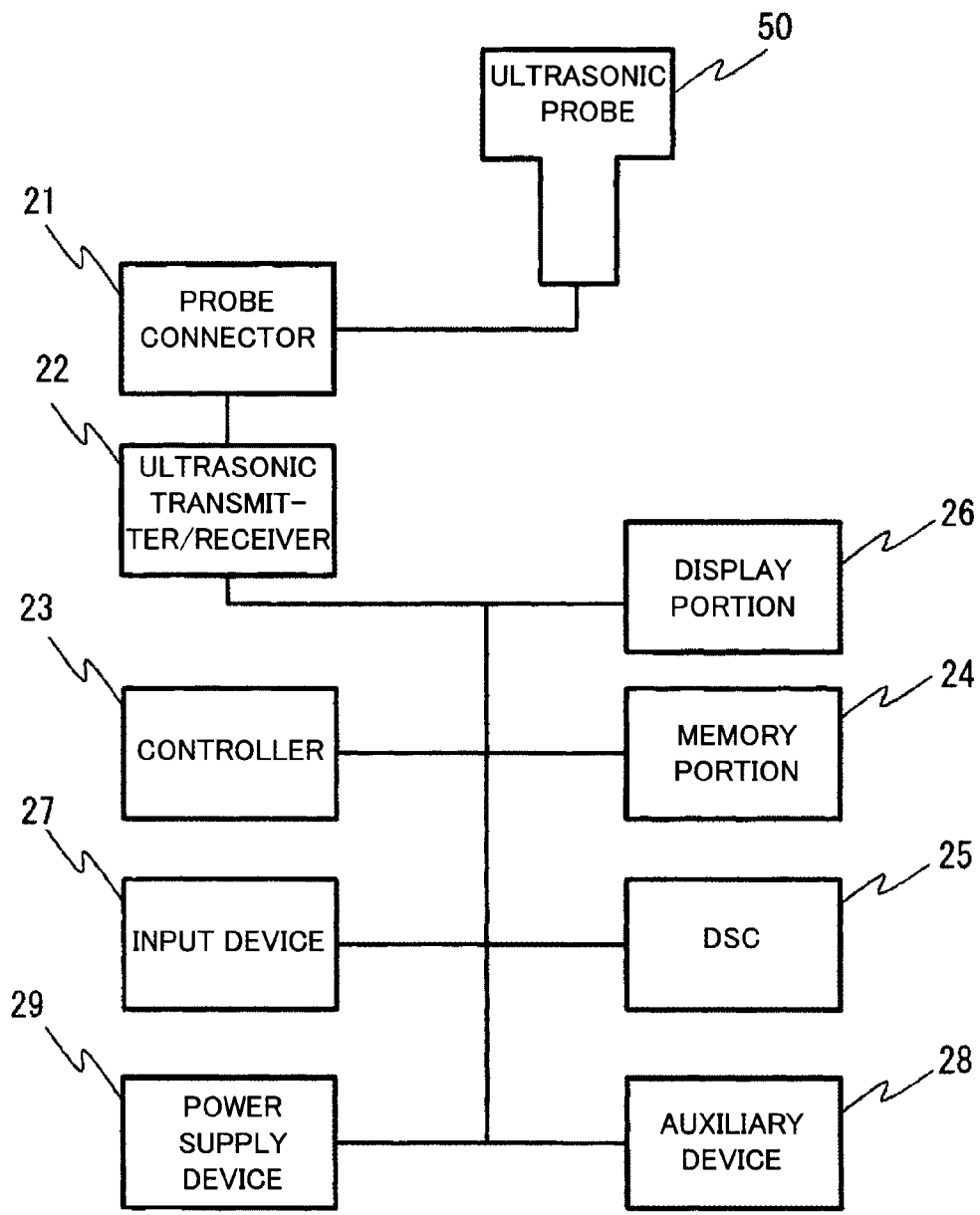
FIG. 2 is a diagram showing one embodiment of a functional configuration of an ultrasonic diagnostic device according to the present invention.

An embodiment in which the present invention is applied to a portable ultrasonic diagnosis device having a biaxial hinge mechanism is described below by reference to FIGS. 1 to 4. FIG. 1 is a perspective diagram showing the appearance of a portable ultrasonic diagnosis device having a biaxial hinge mechanism; FIG. 2 is a block diagram showing a functional configuration of the portable ultrasonic diagnostic device; FIG. 3 shows side views of an example of possible orientation of the portable ultrasonic diagnostic device of FIG. 1; and FIG. 4 is a perspective diagram showing a biaxial hinge mechanism.

The biaxial hinge mechanism means a structure in which portions connected by the hinge mechanism are respectively rotatable with respect to two axes which are orthogonal to each other. In the present embodiment, the two axes are one shaft (tilt shaft) which openably and closably supports a display housing having a display panel with respect to a body of the portable ultrasonic diagnostic device; and the other shaft (pivot shaft) which is used for pivot movement of the display housing.

A portable ultrasonic diagnosis device 100 shown in FIG. 1 includes, as main elements, a display housing (first housing) 10 provided with a display panel 11 such as an LCD; a body housing (second housing) 20 which encloses a main device performing functions required for an ultrasonic measurement; an operation panel housing (third housing) 30 provided with an operation panel 31 on which a keyboard, input buttons, or the like are arranged. The display panel 11 and the operation panel 31 are electrically connected to the device which is enclosed in the body housing 20 by a cable (not shown) or the like.

As shown in FIG. 2, the devices which are required to perform functions of an ultrasonic measurement are, specifically, a probe connecter portion 21 to which an ultrasonic probe 50 is connected, an ultrasonic transmitter/receiver 22, a controller 23, a memory portion 24, a DSC 25, a display portion 26, an input device 27, an auxiliary device 28, and a power supply device 29 or the like. The portable ultrasonic diagnostic device according to the present embodiment mainly includes the probe connecter portion 21, an ultrasonic transmitter/receiver 22, a controller 23, a memory portion 24, a DSC 25, an auxiliary device 28, and a power supply device 29, each enclosed in the body housing 20; a display portion 26 enclosed in the display housing 10; and an input device 27 enclosed in the operation panel housing 30. However, the display portion 26 and the input device 27 can be redundantly provided with the other housings. Further, as the ultrasonic probe 50, various types of probes are available. The ultrasonic probe 50 selected in accordance with an examination target or purpose is used by connecting it to the probe connector portion (202 in FIGS. 1 and 21 in FIG. 2).

The display housing 10 and the operation panel housing 30 are connected at one edge of the body housing 20 respectively via a hinge mechanism 40 such that each can independently change its orientation with respect to the body housing 20. Further, it is also possible to put both housings 10, 30 together and unitedly change the orientation with respect to the body housing 20. The display panel surface 10A of the display housing 10 and the operation panel surface 30A of the operation panel housing 30 have substantially the same size in the vertical and horizontal directions. In a state in which the display panel surface 10A and the operation panel surface 30A are put together in parallel by the hinge mechanism 40 described below, side portions except for a connection portion to the body housing 20 overlap each other with almost no unevenness. It should be noted that, the side surface on the edge of the body housing 20 to which the operation panel housing 30 is connected is called the "front side."

On the edge connected to the body housing 20, the operation panel housing 30 is unitedly provided with more than one arm 33 (four arms in FIG. 1). The arms 33 are bent with respect to the operation panel surface 30A on which the operation panel 31 is provided. A tilt shaft portion (support shaft) 201 which is fixed to the body housing 20 is provided along an axis P1 between two of the arms 33 so as to rotatably support the arms 33. This structure enables the operation panel housing 30 to have an orientation in which the operation panel surface 30A is in parallel to a top surface 20A of the body housing 20 as shown in FIGS. 1 and 3 (a); another orientation in which the operation panel surface 30A is tilted above the body housing 20; and other orientations between these two orientations. In the orientation shown in FIGS. 1 and 3 (a), the bent arms 33 abut against the front surface of the body housing 20, preventing further tilting of the operation panel housing 30. Further, in the orientation shown in FIG. 3 (b), the display panel surface of the display housing 10 prevents further tilting of the operation panel housing 30.

By referring back to FIG. 1, the biaxial hinge mechanism 40 which supports the display housing 10 with the body housing 20 is provided between the center two arms of the four arms 33 of the operation panel housing 30. As shown in FIG. 4, the two axes are a pivot axis Q (41) which makes the display housing 10 pivotable about a vertical axis and a tilt axis P (42) which makes the display housing 10 tiltable about a horizontal axis.

Figure 3A:
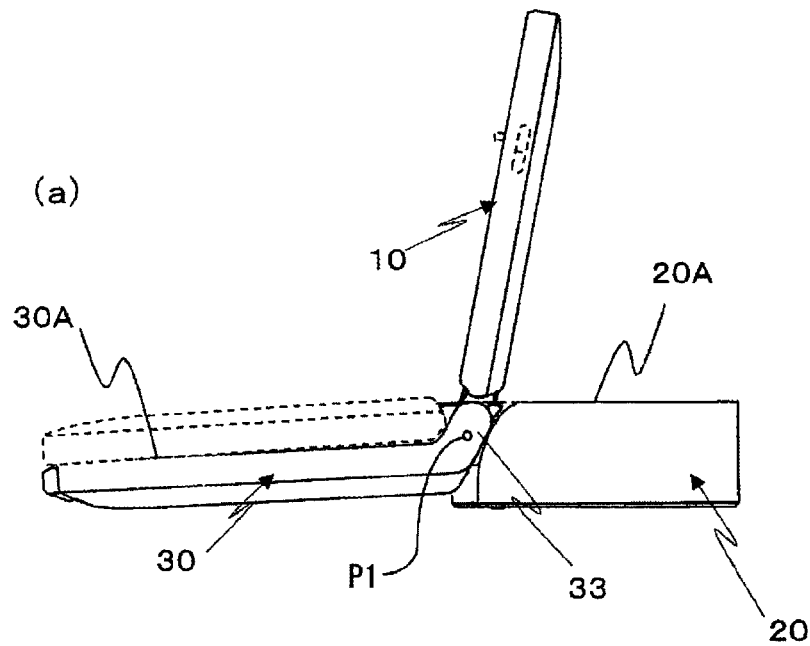
FIGS. 3 (a) and (b) are side views respectively showing one example of orientation of the portable ultrasonic diagnostic device of FIG. 1.
Figure 3B:
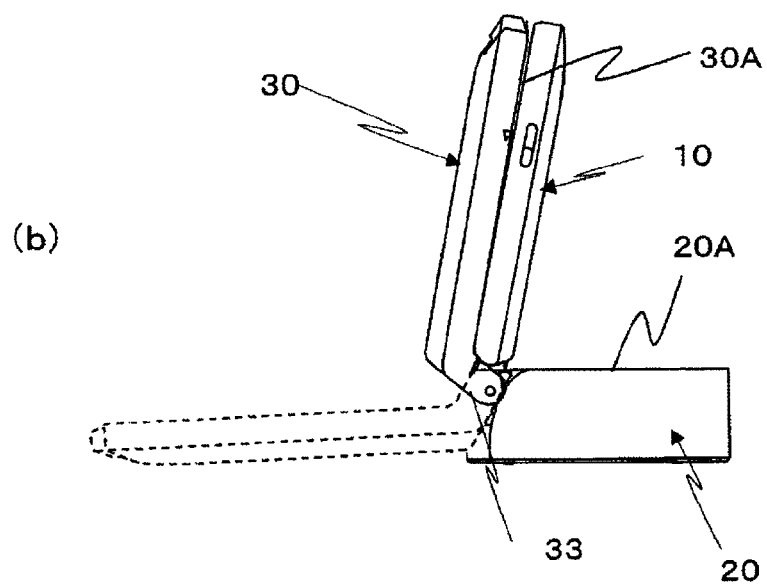
Figure 4:
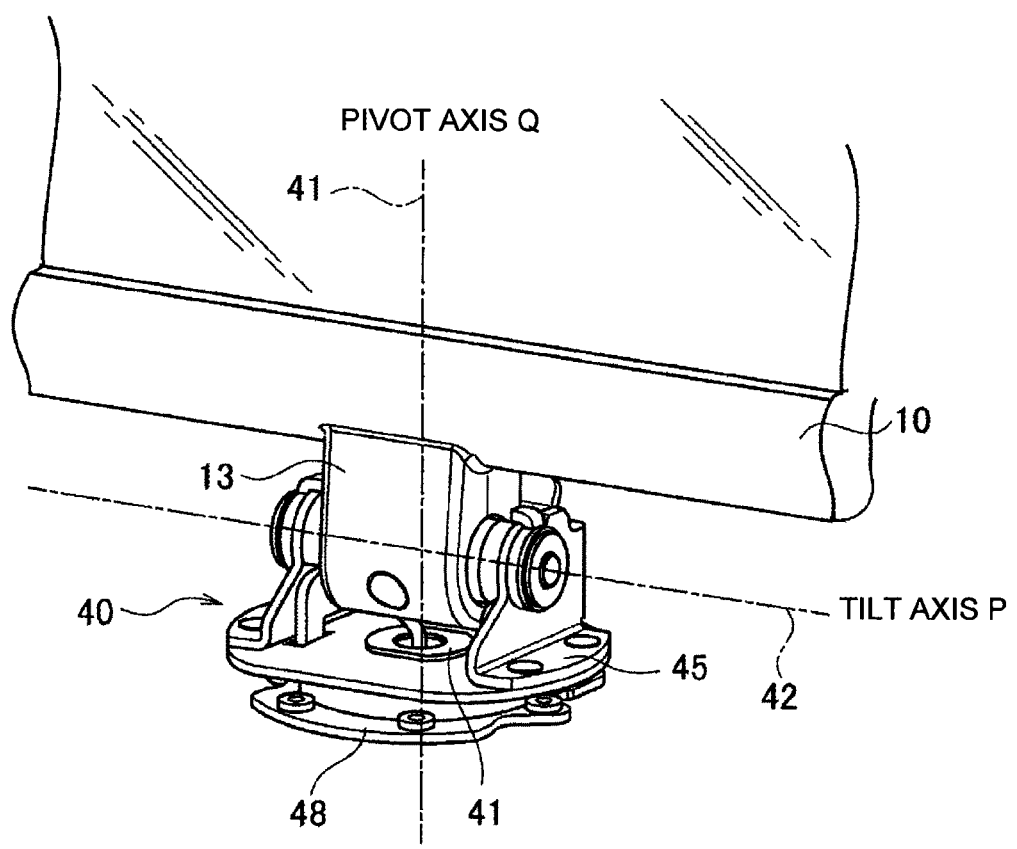
FIG. 4 is a diagram showing main parts of the portable ultrasonic diagnostic device of FIG. 1.
Figure 5A:
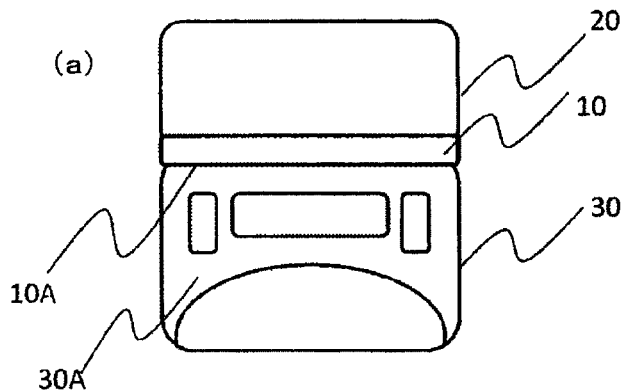
FIGS. 5 (a) to (c) are top views respectively showing a pivoted orientation of a display housing.
Figure 5B:
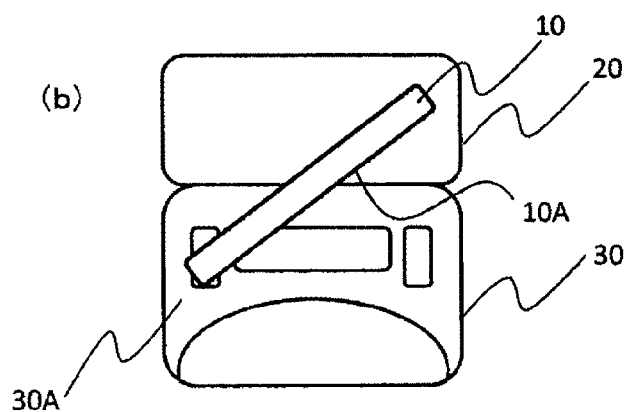
Figure 5C:
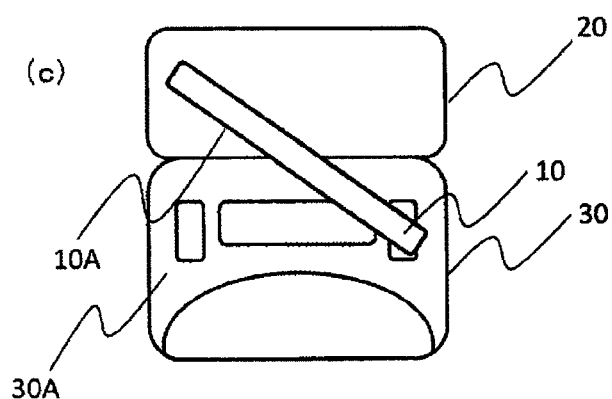

As shown in FIG. 3(a), the tilt movement of the display housing 10 about the tilt axis P includes opening and closing of the display housing 10 between the position shown in the dotted lines and the position shown in the solid lines; and also tilting of the display housing 10 to a desired angle with respect to the horizontal surface. Such a rotation movement is called "tilt" herein. Further, the pivot movement about the pivot axis Q indicates a pivot movement of the display panel surface 10A between the position (called "predetermined position") in which the display panel surface 10A is directed at the front of an operator facing towards the operation panel as shown in FIGS. 1 and 5(a) and a position in which the display panel surface 10A is pivoted at a certain angle with respect to the front of the operation panel as shown in FIGS. 5(b) and (c). This pivot movement is possible not only in a case where the display panel is substantially vertical to the operation panel surface 30A as shown in FIGS. 5(a) to (c) but also in a case where the display panel is tilted with respect to the operation panel surface 30A or the top surface 20A of the body housing 20 at no more than 90 degrees.

The predetermined position indicates the position at which the display housing 10 faces front (front position) as shown in FIG. 1 and FIG. 3(a), and is not pivoted about the pivot axis. In other words, the predetermined position indicates a position of the display housing 10 when opened as indicated in the solid lines as shown in FIG. 3 (a) from a closed position indicated in the dotted lines. The position in which the display housing 10 is opened as shown in the solid lines is a position when the display housing 10 is not pivoted about the pivot shaft (initial position).

Figure 6:
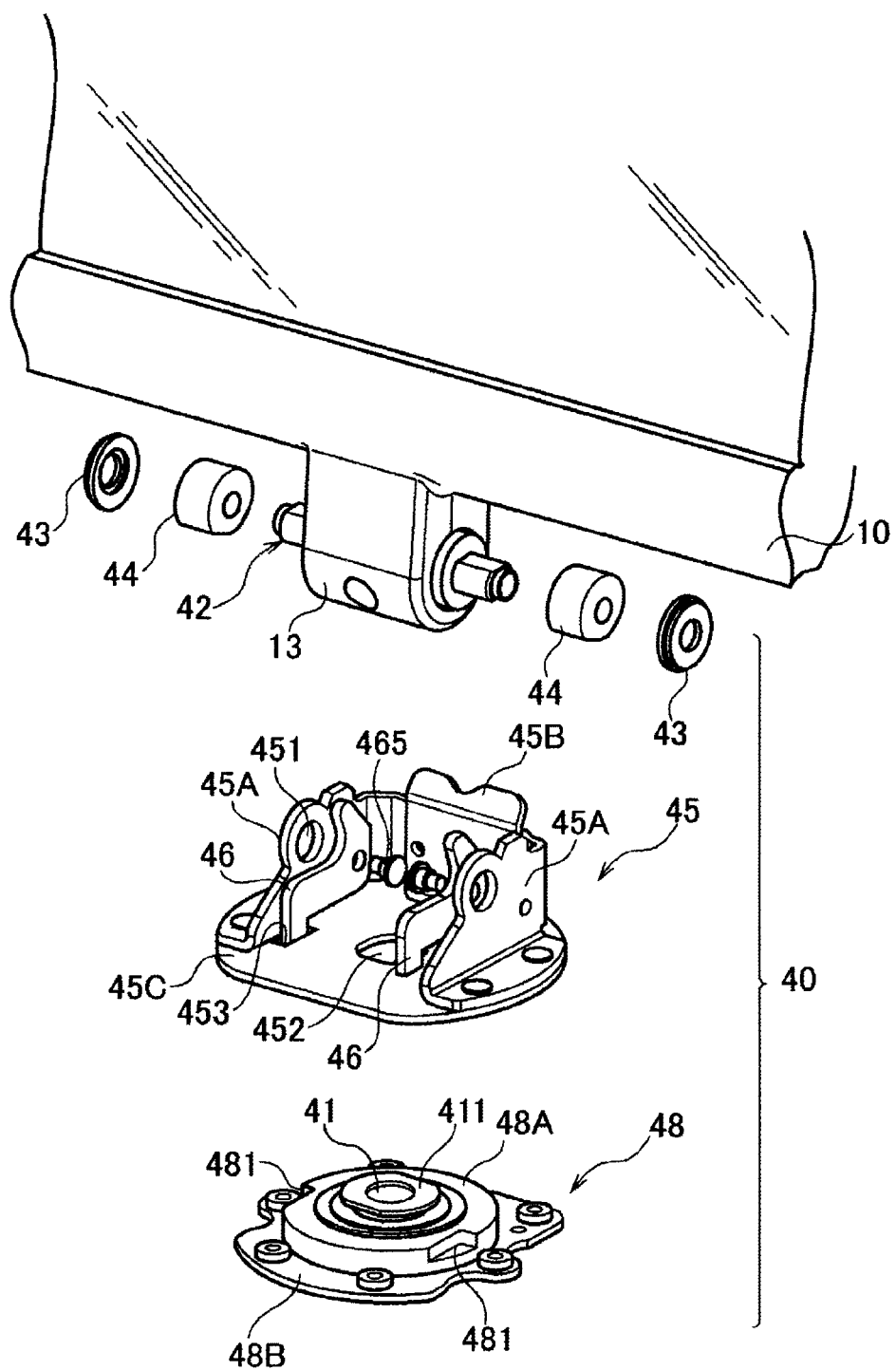
FIG. 6 is an exploded perspective diagram of a support member of a display housing.
Figure 7:
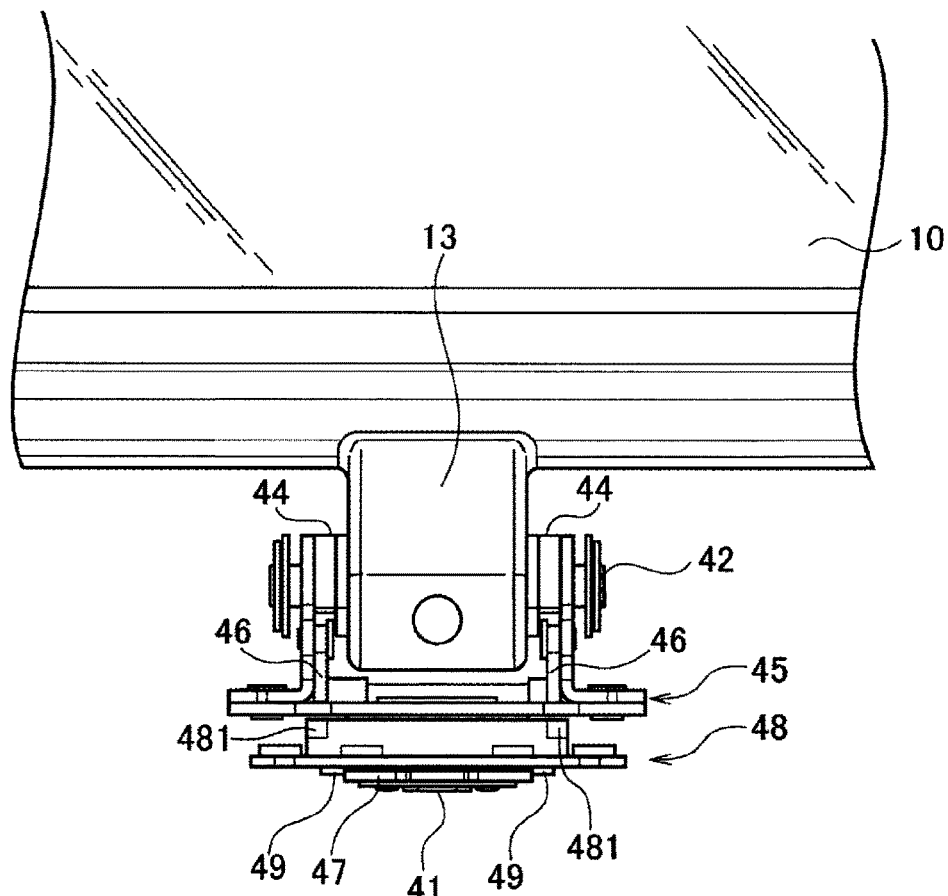
FIG. 7 is a front view of a support member of a display housing.
Figure 8:
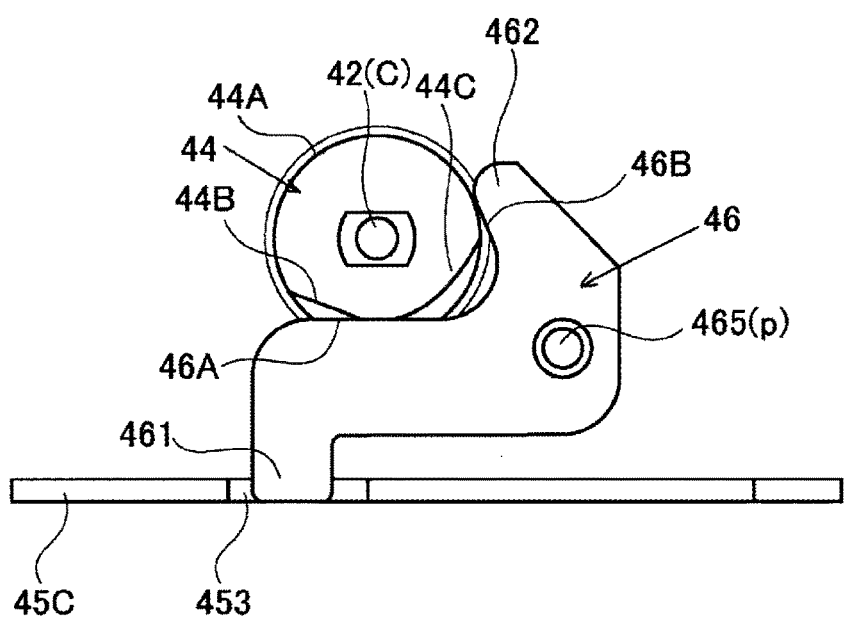
FIG. 8 is a diagram showing shapes of a cam and a stopper included in a support member.

Details about the biaxial hinge mechanism 40 which enables the above movements are described below by reference to FIGS. 6 to 8. FIG. 6 is an exploded perspective diagram of the biaxial hinge mechanism 40; FIG. 7 is a front view of the biaxial hinge mechanism 40; and FIG. 8 is a diagram showing shapes of elements included in the biaxial hinge mechanism 40.

As shown in FIG. 6, the biaxial hinge mechanism 40 is provided with, as basic elements, a tilt shaft 42, a bearing portion 45 of the tilt shaft 42, a pivot shaft 41 fixed to the bearing portion 45, and a base 48 served as a bearing of the pivot shaft 41 in the order from the display housing 10 side. The base 48 is fixed to an element inside the body housing 20. The biaxial hinge mechanism 40 according to the present embodiment is further provided with, as characteristic elements, a tilt limit mechanism (cams 44, stoppers 46, and notches 481 on the top surface of the base) and a pivot limit mechanism (a disc plate 47 and stopper shafts 49).

The tilt shaft 42 is fixed to an arm 13 provided at the center portion of the display housing 10 in the horizontal direction at the edge portion which is connected to the body housing 20. The tilt shaft 42 is provided with the cams 44 included in the tilt limit mechanism. The cams 44 are fixed to the tilt shaft 42 with the arm 13 sandwiched therebetween. Each of the cams 44 has a short cylindrical shape in the shaft direction. A cam surface is formed on the outer circumferential surface of each cam 44. The cam surface has a shape as if a part of the cylindrical outer circumferential surface is cut off by a surface in parallel to the shaft such that the cams 44 form the tilt limit mechanism with the stoppers 46 which engage with the cam surfaces and are disposed on the bearing portion 45 and further with the notches 481 which are disposed on the top surface of the base 48.

The bearing portion (first bearing portion) 45 rotatably supports the tilt shaft 42. As shown in FIG. 6, the bearing portion 45 includes two opposing side plates 45A; a rear plate 45B connecting the side plates 45A; and a bottom plate 45C having a flat bottom surface on which the side plates 45A and the rear plate 45B are fixed. Each of the side plates 45A includes an opening 451 formed thereon for supporting the tilt shaft 42 such that the tilt shaft 42 is rotatably fixed through the openings 451. It should be noted that, although not shown in FIG. 6, a limit plate is provided between the cam 44 and the washer 43 to limit a rotatable range of the tilt shaft 42.

Each of the limit plates has a bent portion formed on the outer circumference. The rotatable range of the tilt shaft 42 is limited by the bent portion which abuts against the top surfaces of the side plates 45A of the bearing portion 45. By the structure including the tilt shaft 42 and the bearing portion 45, the display housing 10 to which the tilt shaft 42 is fixed via the arm 13 is made tiltable in a predetermined range such as about 100 degrees about the tilt shaft 42, from an orientation in which the display panel surface is substantially horizontal to an orientation in which the display panel surface is substantially vertical.

An opening 452 through which the pivot shaft 41 is fixed is formed on the bottom plate 45C of the bearing portion 45. The pivot shaft 41 includes a flange portion 411 formed on one end of the cylindrical shaft such that the pivot shaft 41 is fixed to the bearing portion 45 by clamping the flange portion 411 over the opening 452 of the bearing portion 45. The shaft portion of the pivot shaft 41 is pivotably supported in a through hole (second bearing portion) formed on the base 48 which is fixed to the body housing 20.

Each of the side plates 45A of the bearing portion 45 is provided with a stopper 46 which is rotatably supported by a stopper rotation shaft 465. Each stopper 46 is a thin plate member which has, in the thickness direction, a curved surface against which the cam surface of each cam 44 abuts.

The shape of the stopper 46 and the cam surface of the cam 44 are shown in FIG. 8. As shown in FIG. 8, the stopper 46 is a plate member which is bent at two portions. At one of the two bent portions, the stopper 46 is rotatably supported on the bearing portion 45 by the stopper rotation shaft 465. The stopper 46 includes a portion extending from a supporting point p in the horizontal direction in FIG. 8 to the other bent portion; a portion extending obliquely upward from the supporting point p; one free end 461 extending downward from the other bent portion; and the other free end 462 at the end of the portion extending obliquely upward from the supporting point p. The curved surface with which each cam 44 engages includes an upper surface 46A of the portion horizontally extending from the supporting point p and a side surface 46B of the portion extending obliquely upward from the supporting point p.

The cross-section of the cam 44 includes an arc portion having a constant distance (radius) from the center c of the tilt shaft 42 and other portions which are two chords having a radius smaller than the arc portion. The cam surface continuously having such a cross-section in the shaft direction of the tilt shaft 42 includes a cylindrical cam surface 44A corresponding to the arc portion, and flat cam surfaces 44B, 44C.

The cam surface 44A rotates the stopper 46. Specifically, the tilt shaft 42 is rotated counter-clockwise in FIG. 8 by closing the display housing 10. When reaching the upper surface 46A of the stopper 46, the cam surface 44A pushes the upper surface 46A causing the stopper 46 to rotate counter-clockwise. On the contrary, by opening the display housing 10 from the closed state, the tilt shaft 42 is rotated clockwise. When reaching the side surface 46B of the stopper 46, the cam surface 44A pushes the side surface 46B, causing the stopper 46 to rotate clockwise until the stopper 46 is returned to the position shown in FIG. 8.

It should be noted that the movement of the stopper 46 by the cam surface 44A described above is possible only when each notch 481 on the top surface of the base 48 described below and the free end 461 of each stopper 46 are at a position in the pivotable direction where they can be engaged with each other. On the contrary, when the stopper 46 is stopped at a position in the pivotable direction shown in FIG. 8, the stopper 46 prevents counter-clockwise rotation of the cam 44.

One of the free ends 461 (first end portion) of the stopper 46 which is not supported by the stopper rotation shaft 465 is placed inside a through-hole 453 formed on the bottom plate 45C and in contact with the top surface of the base 48.

The base 48 includes a disc portion 48A having a sliding surface which is in surface contact with the bottom plate 45C of the bearing portion 45 and further includes a bottom plate portion 48B which is unitedly provided with the disc portion 48A. The bottom plate portion 48B is fixed to an element within the body housing 20 by means of a screw or the like. The top surface of the disc portion 48A is a flat surface which is in parallel to the bottom surface of the bottom plate 45C of the bearing portion 45; and includes two notches 481 formed thereon. The notches 481 are formed at positions such that the notches 481 are positioned directly below a pair of through-holes 453 formed on the bottom plate 45C of the bearing portion 45 when the bearing portion 45 is at the predetermined position in the pivotable direction of the pivot shaft; in other words, when the front surface of the display panel surface 10A of the display housing 10 which is coupled with the bearing portion 45 faces the front surface of the operation panel.

As described above, the free end 461 of each stopper 46 rotationally supported on the bearing portion 45 is inserted into the through-hole 453 of the bottom plate 45C, such that the stopper 46 is rotatable because the free end can fall into the notch 481 when the bearing portion 45 is at the predetermined position in the pivotable direction of the pivot shaft. On the other hand, when the bearing portion 45 is at a position pivoted from the predetermined position in the pivotable direction of the pivot shaft, because the free end 461 of each stopper 46 is kept to abut against the flat top surface of the disc portion 48A, the free end 461 is prevented from rotating further below the top surface (counter-clockwise in FIG. 8).

Based on the structure of the biaxial hinge mechanism 40 described above, movements of the display housing 10 are described below. First, tilting movement is described by reference to FIG. 9. When the display housing 10 is at the predetermined position in the pivotable direction of the pivot shaft (FIG. 5(a)), each stopper 46 rotatably supported by the bearing portion 45 is positioned such that the free end 461 is directly above the notch 481 formed on the top surface of the disc portion 48A of the base 48 as shown in FIG. 9(a). At this predetermined position in the pivotable direction of the pivot shaft, when the display housing 10 is vertically orientated (opened) with respect to the body housing 20, each cam 44 fixed to the tilt shaft 42 is positioned such that the cylindrical cam surface 44A is positioned at the upper side (the display housing side), while the border between the cam surfaces 44B, 44C which are two flat surfaces abuts against the upper surface 46A of the stopper 46. The cylindrical cam surface 44A near the border with the cam surface 44C abuts against the side surface 46B of the stopper 46.

When the display housing 10 is tilted towards the operation panel housing, the tilt shaft 42 fixed to the display housing 10 (arm 13) and the cam 44 fixed thereto are unitedly rotated. The rotation direction is counter-clockwise in FIG. 9(a). By the rotation of the cam 44, the cam surface abutting against the upper surface of the stopper 46 is changed from the cam surface 44B to the cam surface 44A; and the cam surface 44c moves onto the side surface 46B of the stopper 46. Because the radius of the cam surface 44A is larger than the radius of the cam surface 44B, the stopper 46 is pushed further down by the cam surface 44A so as to rotate the stopper 46 about the stopper rotation shaft 465 until the free end 461 falls down within the notch 481 formed on the base 48. In other words, at the predetermined position in the pivotable direction of the pivot shaft, the display housing 10 can be rotated until the display housing 10 is closed as shown in FIG. 9(b).

With the display housing 10 in the closed position, because the free end 461 of the stopper 46 engages with the notch 481 on the top surface of the base 48, the pivot movement about the pivot shaft; in other words, the pivot of the bearing portion 45 with respect to the base 48 about the pivot shaft 41, is prevented. When the display housing 10 is tilted to be opened (clock-wise in FIG. 9), the cam surface 44c abutting against the side surface 46B of the stopper 46 is changed to the cam surface 44A having a larger radius such that the stopper 46 (free end 462 side) is rotated in the same direction. In this way, because the free end 461 having engaged with the notch 481 returns to the position shown in FIG. 9(a), the display housing 10 (bearing portion 45) can be freely pivotable about the pivot shaft.

On the other hand, when the display housing 10 is pivoted for a certain angle from the predetermined position in the pivotable direction of the pivot shaft as shown in FIGS. 5(b) and (c), the end 461 of each stopper 46 is placed on the top surface of the disc portion 48A of the base 48 (in a state without the notch 481 in FIG. 9(a) such that the stopper end 461 is in contact with the top surface of the disc portion) such that the stopper 46 cannot be further rotated counter-clockwise. Therefore, when the display housing 10 is pivoted from the predetermined position, although the display housing 10 can be pivoted and closed until the cam surface 44B of the cam 44 abuts against the upper surface 46A of the stopper 46, further pivoting is prevented by the stopper 46. In this way, when an attempt is made to close the display housing 10 at a position other than the predetermined position in the pivotable direction, the closing movement is prevented such that the display housing 10 is prevented from coming into collision with other elements.

The pivotable angle is limited when the display housing is at an angle no greater than θ where the tilt angle of the tilt shaft is assumed to be 0 degrees when the display housing is closed and the minimum tilt angle of the tilt shaft at which the display housing does not interfere with other portions of the portable ultrasonic diagnostic device is assumed to be θ. This angle can be adjusted by arranging the shape of the cam surface.

It should be noted that, because it is possible to tilt the display housing 10 to some degree in such a state (until the cam surface 44B of the cam 44 and the upper surface 46A of the stopper abut against each other), closing movement is allowed regardless of the position in the pivotable direction of the pivot axis. Therefore, when the display housing 10 cannot be closed beyond some extent, the display housing 10 can be closed after pivoting the display housing 10 back to the predetermined position such that each stopper 46 is rotated to have the free end 461 engaged with the notch 481 of the base 48. Because such an operation can be performed by pivoting the display housing 10 about the pivot shaft while pushing the display housing 10 in the closing direction, the operation can be easily performed in dark places such as in darkrooms or in such a situation that attention is caught by a patient or others. Therefore, the display panel can be reliably prevented from interfering with other elements and causing damage.

Figure 10:
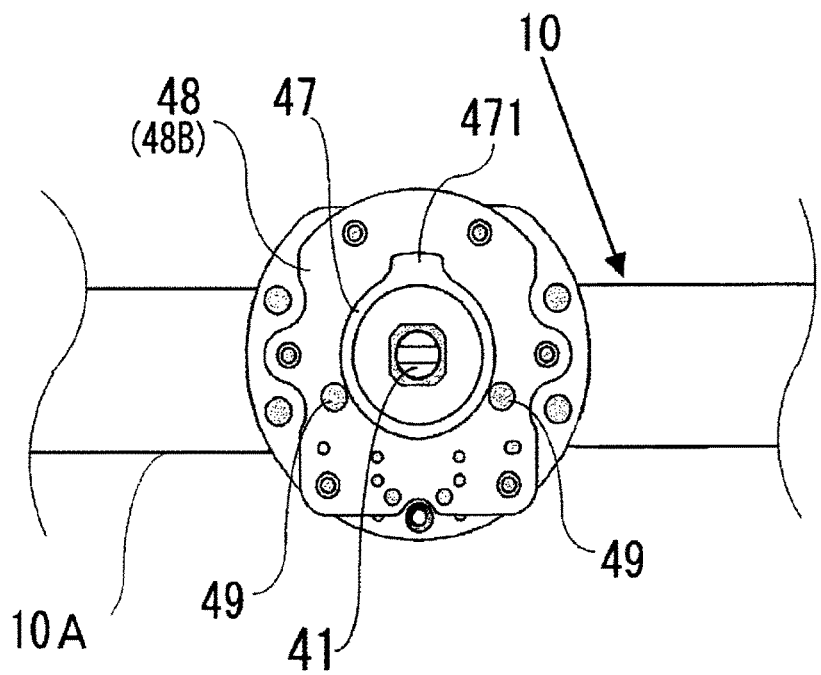
FIG. 10 is a diagram showing a predetermined position of a pivot shaft in a pivotable direction.
Figure 11:
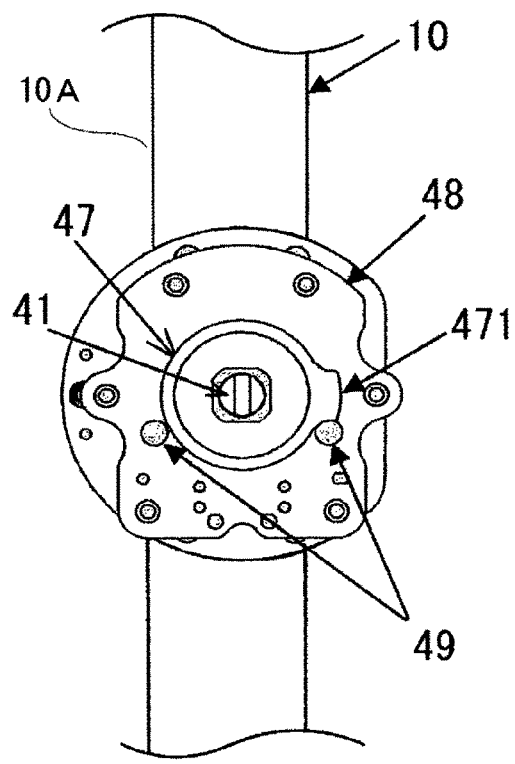
FIG. 11 is a diagram showing a position of a pivot shaft pivoted 90 degrees from the predetermined position.

Next, pivot operation of the display housing 10, in particular, the pivot limit mechanism is described below by reference to FIGS. 10 and 11. FIGS. 10 and 11 show the base 48 viewed from the bottom. FIG. 10 is for the predetermined position in the pivotable direction of the pivot shaft; and FIG. 11 is for the position pivoted 90 degrees.

The pivot limit mechanism is formed by a disc plate 47 fixed to an end of the pivot shaft 41 and stopper shafts 49 formed on the bottom plate portion 48B of the base 48. The disc plate 47 is fixed to the end of the pivot shaft 41 which penetrates through the base 48. A convex portion 471 projected from the outer circumference of the disc is formed. Further, on the back surface (bottom plate portion 48B) of the base 48, a pair of stopper shafts 49 are provided in vertical to the back surface (refer to FIG. 7). The stopper shafts 49 are fixed at positions where the stopper shafts 49 are in contact with the outer circumferential surface when the disc plate 47 rotates together with the pivot shaft 41 such that the rotation of the disc plate 47 is stopped by the convex portion 471 of the rotating disc plate 47 abutting against one of the stopper shafts 49. The pivotable range of the pivot shaft 41 is determined by the angle which is formed by two linear lines connecting the center of the pivot shaft 41 and the centers of the two stopper shafts 49. In the present embodiment, the stopper shafts 49 are arranged such that the pivotable range of the pivot shaft 41 is ±90 degrees where the angle is assumed to be 0 degrees when the display housing 10 is at the predetermined position.

When the display housing 10 is pivoted, for example, 90 degrees to the right from the position shown in FIG. 10, the bearing portion 45, the pivot shaft 41 fixed to the bearing portion 45, and the convex portion 471 of the disc plate 47 fixed at an end of the pivot shaft 41 are pivoted together with the display housing 10 such that pivot of the display housing 10 is stopped by the convex portion 471 abutting against the stopper shaft 49 on the right as shown in FIG. 11. Therefore, in order to pivot the display panel 90 degrees in the pivotable direction as generally desired, the operator does not need to adjust the position but the position where pivot is prevented is the 90 degrees pivoted position.

Similarly, when pivoting the display housing 10 90 degrees to the left from the position shown in FIG. 10, the pivot is stopped by the convex portion 471 abutting against the stopper shaft 49. In this way, the display housing 10 is pivotable within a pivotable range determined by the positional relationship between the convex portion 471 and the stopper shafts 49. This prevents an accident of twisting and cutting the cable running through the support member between the display housing 10 and the body housing 20 due to repeated pivot movements.

When the display housing 10 is in the closed orientation; that is, when the free end 461 of each stopper 46 engages with the notch 481 of the base 48 (FIG. 9(b)), pivoting is prevented by the engagement of the end 461 and the notch 481. On the contrary, when the display housing 10 is opened such that the free end 461 is on the top surface of the base 48 (FIG. 9(a)), the engagement between the ends 461 of the stopper 46 and the notch 481 is released, allowing pivoting in ±90 degrees. In other words, according to the structure of the present embodiment, free pivot within ±90 degrees is possible in any orientation other than the closed orientation.

As described above, the portable ultrasonic diagnostic device according to the present embodiment includes a first housing (display housing 10) provided with a display panel; and a second housing (body housing 20 or operation panel housing 30); and a support member 40 which includes a tilt shaft and a pivot shaft orthogonal to the tilt shaft and supports the first housing 10 such that the first housing 10 is tiltable with respect to the second housings 20, 30 and pivotable. The support member 40 is provided with a tilt limit mechanism to prevent the tilting of the first housing 10 at a position other than the predetermined position in the pivotable direction of the pivot shaft.

According to the portable ultrasonic diagnostic device of the present embodiment, because the display housing can be completely closed by rotating the tilt shaft 42 only when the display housing is at the predetermined position in the pivotable direction of the pivot shaft, while tilting is prevented at a position other than the predetermined position, a problem that the display housing collides with other elements when closed while being pivoted over a predetermined angle can be avoided.

Further, the portable ultrasonic diagnostic device of the present embodiment allows rotation of the tilt shaft 42 within a limited rotatable range when the first shaft 10 is at a position other than the predetermined position. Therefore, because closing operation is allowed to some extent even when the display housing is pivoted at a certain angle, closing operation can be performed without paying attention to the position of the display housing in the pivotable direction by performing the closing operation and the pivot operation at the same time.

The portable ultrasonic diagnostic device of the present embodiment has the following other main features. The support member supporting the first housing includes a tilt shaft fixed at an edge portion of the first housing; a first bearing portion 45 which integrally rotates with the pivot shaft and rotatably supports the tilt shaft; and a second bearing portion 48 which rotatably supports the pivot shaft 41. The tilt limit mechanism includes, on the first bearing portion 45, stoppers 46 rotatably supported by the shaft 465 which is in parallel with the tilt shaft 42, and notches 481 which are provided on the second bearing portion 48, each notch 481 engaging with an end portion 461 of each stopper 46. The stoppers 46 limit the rotation of the tilt shaft 42 when the stoppers 46 are at a position where the stoppers 46 do not engage with the notches 481.

The notches 481 are positioned such that the notches 481 can engage with the stoppers 46 when the tilt shaft 42 is at the predetermined position in the pivotable direction of the pivot shaft; while the notches 481 cannot engage with the stoppers 46 when the tilt shaft 42 is at a position other than the predetermined position.

The tilt limit mechanism is further provided with cams 44, each of which unitedly rotates with the tilt shaft 42. The cam surface of each cam 44 abuts against the stopper 46 to rotate the stopper 46 between a first position where the stopper 46 engages with the notch 481 and a second position where the stopper 46 does not engage with the notch 481.

Further, the portable ultrasonic diagnostic device of the present embodiment is provided with a pivot limit mechanism which limits the pivotable angle of the first housing to ±90 degrees where the pivot angle is assumed to be 0 degrees when the first housing is at the predetermined position in the pivotable direction of the pivot shaft. The pivot limit mechanism includes a convex portion 471 which is fixed to the pivot shaft 41 and unitedly rotates with the pivot shaft; and a pair of stop members (stopper shafts) 49 which are fixed to the bearing portion (base) 48 of the pivot shaft 41 and stops the rotation of the convex portion 471.

According to the portable ultrasonic diagnostic device of the present embodiment, it is possible, by providing the pivot limit mechanism, to prevent damage to a cable which electrically connects the device within the display housing and the device within the body housing caused by pivoting.

It should be noted that the portable ultrasonic diagnostic devices according to the present invention are not limited to those in the above described embodiments, and various changes are possible.

For example, although a device including both the tilt limit mechanism and the pivot limit mechanism is described in the above embodiments, the present invention covers a portable ultrasonic diagnostic device which includes either one of the two limit mechanisms. As an important feature of the portable ultrasonic diagnostic device according to the present invention is to be provided with the tilt limit mechanism and/or the pivot limit mechanism, any portable ultrasonic diagnostic devices which do not include the other features are covered by the present invention.

Further, although, in the above embodiments, an example of the present invention applied to a portable ultrasonic diagnostic device having a structure which is provided with the three housings (the display housing, the operation panel housing, and the body housing), and in which the display housing and the operation panel housing are coupled at one edge of the body housing, the present invention is also applicable to a portable ultrasonic diagnostic device which consists of the display housing and the body housing.

REFERENCE NUMERALS

10 display housing (first housing), 10A display panel surface, 11 display panel, 20 body housing (second housing), 201 support shaft, 30 operation panel housing (third housing), 30A operation panel surface, 31 operation panel, 40 biaxial hinge mechanism (support member), 41 pivot shaft, 42 tilt shaft, 44 cam (tilt limit mechanism), 45 bearing portion (first bearing portion), 46 stopper (tilt limit mechanism), 47 disc plate (pivot limit mechanism), 471 convex portion (pivot limit mechanism), 48 base (second bearing portion), 481 notch (tilt limit mechanism), 49 stopper shaft (pivot limit mechanism).

The invention claimed is:

1. A portable ultrasonic diagnostic device comprising:
a first housing provided with a display panel;
a second housing; and
a support member having:
   a tilt shaft fixed to an edge portion of the first housing;
   a pivot shaft orthogonal to the tilt shaft;
   a first bearing portion which unitedly pivots with the pivot shaft and rotatably supports the tilt shaft;
   a second bearing portion which pivotably supports the pivot shaft;
   a stopper rotatably supported in the first bearing portion in parallel to the tilt shaft; and
   a notch which is provided with the second bearing portion and engages with an end of the stopper,
wherein the support member supports the first housing such that the first housing is tiltable and pivotable with respect to the second housing, and
wherein the stopper limits the rotation of the tilt shaft when the stopper is at a position where the stopper does not engage with the notch in a pivotable direction of the pivot shaft.

2. The portable ultrasonic diagnostic device according to claim 1, wherein the stopper does not engage with the notch when the first housing is pivoted about the pivot shaft.

3. The portable ultrasonic diagnostic device according to claim 1, wherein
the second housing comprises a third housing provided with an operation panel, and
the third housing is connected to the second housing such that the third housing is tiltable about a support shaft orthogonal to the pivot shaft.

4. The portable ultrasonic diagnostic device according to claim 3, wherein the stopper does not engage with the notch where the first housing is positioned with respect to the second housing in the pivotable direction of the pivot shaft such that the tilt shaft and the support shaft are not in parallel.

5. The portable ultrasonic diagnostic device according to claim 4, wherein the stopper limits rotation of the tilt shaft to be within a limited rotatable range of the tilt shaft when the stopper is at the position where the stopper does not engage with the notch.

6. The portable ultrasonic diagnostic device according to claim 1, wherein the notch is arranged at a position where the notch is engageable with the stopper when the tilt shaft is at a predetermined position in the pivotable direction of the pivot shaft and not engageable with the stopper when the tilt shaft is at a position other than the predetermined position.

7. The portable ultrasonic diagnostic device according to claim 1, wherein the support member further comprises a cam which unitedly rotates with the tilt shaft, and
wherein a cam surface of the cam abuts against the stopper such that the cam rotates the stopper between a first position where the stopper engages with the notch and a second position where the stopper does not engage with the notch.

8. The portable ultrasonic diagnostic device according to claim 1, wherein stopper limits a rotatable range of the tilt shaft to a range between 0 degrees to (180-θ) degrees where a rotation angle of the tilt shaft is defined to be 0 degrees when a panel surface of the display panel is in parallel to a main flat surface of the second housing and a minimum angle at which the first housing does not interfere with other elements of the portable ultrasonic diagnostic device is defined to be θ degrees.

9. The portable ultrasonic diagnostic device according to claim 1, wherein
a pivot limit mechanism which limits pivoting of the first housing is provided, and
the pivot limit mechanism limits a pivotable angle to ±90 degrees where a pivot angle of the first housing is defined to be 0 degrees when the first housing is at a predetermined position in the pivotable direction of the pivot shaft.

10. The portable ultrasonic diagnostic device according to claim 1, further comprising:
a convex portion which is fixed to the pivot shaft and unitedly pivots with the pivot shaft; and
a pair of stop members which are fixed to the second bearing portion, the pair of stop members stops pivot of the convex portion to limit pivoting of the first housing.

11. A portable ultrasonic diagnostic device comprising:
a first housing provided with a display panel;
a second housing; and
a third housing provided with an operation panel, the third housing being tiltably connected to the second housing via a support shaft;
a pivot shaft which pivots the first housing about an axis orthogonal to the support shaft;
a tilt shaft which rotates the first housing about an axis orthogonal to the pivot shaft; and
a support member which supports the first housing to the second housing,
wherein the support member comprises a first bearing portion which rotatably supports the tilt shaft and unitedly pivots with the pivot shaft and a second bearing portion which pivotably supports the pivot shaft and is in surface contact with the first bearing portion,
the first bearing portion comprises a stopper which is rotatable about an axis in parallel to the pivot shaft,
the second bearing portion comprises a notch on a surface in contact with the first bearing portion, the notch engaging with the stopper at a rotation position of the stopper where the tilt shaft and the support shaft are in parallel, and
a limit of a rotatable range of the tilt shaft is released by the engagement of the stopper and the notch.

12. The portable ultrasonic diagnostic device according to claim 11, wherein
the tilt shaft comprises a cam which unitedly rotates with the tilt shaft and includes a cam surface formed on an outer circumferential surface,
the cam surface of the cam engages with the stopper to rotate the stopper between a first position where the stopper engages with the notch and a second position where the stopper does not engage with the notch.

13. The portable ultrasonic diagnostic device according to claim 11, further comprising:
a convex portion which is fixed to the pivot shaft and unitedly pivots with the pivot shaft; and
a pair of stop members which are fixed to the second bearing portion, the pair of stop members stops pivot of the convex portion to limit pivoting of the first housing.

* * * * *